United States Patent [19]

Kaufman et al.

[11] 4,358,571

[45] Nov. 9, 1982

[54] CHEMICALLY MODIFIED IMIDAZOLE CURING CATALYSTS FOR EPOXY RESIN AND POWDER COATINGS CONTAINING THEM

[75] Inventors: Marvin L. Kaufman; George F. Salathe, both of Bridgewater, N.J.

[73] Assignee: Mobil Oil Corporation, New York, N.Y.

[21] Appl. No.: 242,216

[22] Filed: Mar. 10, 1981

[51] Int. Cl.$^3$ .................... C08G 59/50; C07D 233/60; C09D 3/58

[52] U.S. Cl. .................................... 525/524; 427/185; 427/195; 427/386; 525/507; 525/529; 528/94; 528/117; 528/365; 548/335; 548/336; 548/342; 548/346

[58] Field of Search .................. 427/185, 195, 386; 525/507, 529, 524; 528/94, 117, 365, 408; 548/335, 336, 342, 346

[56] References Cited

U.S. PATENT DOCUMENTS

| | | | |
|---|---|---|---|
| 3,356,645 | 12/1967 | Warren | 548/342 X |
| 3,418,333 | 12/1968 | Warren | 548/342 X |
| 3,549,653 | 12/1970 | Beaman et al. | 548/336 |
| 3,553,166 | 1/1971 | Anderson | 528/117 |
| 3,562,213 | 2/1971 | Collis | 528/94 X |
| 3,677,978 | 7/1972 | Dowbenko et al. | 548/336 X |
| 3,746,684 | 7/1973 | Marshall et al. | 528/117 X |
| 3,816,366 | 6/1974 | Laudise | 260/23 EP |
| 3,896,082 | 7/1975 | Rensmann et al. | 528/94 |
| 4,000,781 | 1/1977 | Knapp | 427/386 X |
| 4,066,625 | 1/1978 | Bolger | 260/59 R |
| 4,069,203 | 1/1978 | Carey et al. | 528/94 |
| 4,205,156 | 5/1980 | Sawa et al. | 528/117 |

FOREIGN PATENT DOCUMENTS

| | | |
|---|---|---|
| 2609361 | 9/1977 | Fed. Rep. of Germany . |
| 2744721 | 4/1979 | Fed. Rep. of Germany . |
| 1215683 | 12/1970 | United Kingdom . |
| 1266016 | 3/1972 | United Kingdom . |
| 1366603 | 9/1974 | United Kingdom . |

OTHER PUBLICATIONS

Chemical Abstracts, vol. 75, 1971, Article 35884s.

*Primary Examiner*—Thurman K. Page
*Attorney, Agent, or Firm*—Charles A. Huggett; Hastings S. Trigg; George W. Allen

[57] ABSTRACT

Imidazole or substituted imidazole is adducted with acrylate ester, an epoxy, or an isocyanate followed by neutralization with lower fatty acid or alkylene or aromatic dicarboxylic acid. The product is a curing agent which is combined with an epoxy resin to form a powder coating.

15 Claims, No Drawings

CHEMICALLY MODIFIED IMIDAZOLE CURING CATALYSTS FOR EPOXY RESIN AND POWDER COATINGS CONTAINING THEM

BACKGROUND OF THE INVENTION

1. Field of the Invention

This invention is concerned with epoxy powder coating formulations and with curing agents therefor.

2. Description of the Prior Art

It has been proposed to cure epoxy resins, such as diglycidyl ethers of bisphenol A, with imidazoles having no substituents or lower alkyl substituents. See, for example, "Handbook of Epoxy Resins", Lee and Neville, Chapter 10, page 17, McGraw-Hill (1967). Insofar as is now known, chemically modified imidazoles disclosed herein have not been proposed to cure epoxy resins. Such modified imidazoles are advantageous in providing relatively short cure times at low cure temperatures and improved package stability.

SUMMARY OF THE INVENTION

This invention provides curing agents for epoxy resins that comprise an imidazole having the formula:

$$\begin{array}{c} N\text{---}C\text{---}Y \\ \parallel \quad \parallel \\ X\text{---}C \quad C\text{---}Z \\ \diagdown \diagup \\ N \\ H \end{array}$$

wherein X, Y and Z are the same or different and can be hydrogen, halogen, or an organic radical such as a hydrocarbon or substituted hydrocarbon radical, e.g. alkyl, phenyl, aralkyl, alkenyl, cycloalkyl, cycloalkenyl, or alkaryl, having up to 15 carbon atoms, modified by addition of a $C_1$–$C_{18}$ alkyl aryl, cycloalkyl, aralkyl, or hydroxyalkyl (meth)acrylate, by addition of a diglycidyl ether of a bisphenol, by addition of a mono or polyglycidyl ether of a mono or polyalcohol or a mono or polyphenol, or by carbamoylation; followed by neutralization with a lower fatty acid, a lower alkylene dicarboxylic acid, or an aromatic polycarboxylic acid.

It also provides a powder coating comprising at least one diglycidyl ether of a bisphenol and the aforesaid curing agent.

DESCRIPTION OF THE SPECIFIC EMBODIMENTS

The imidazoles utilizable in preparing the curing agents of this invention are known and many are commercially available compounds. Typical imidazoles include imidazole; 2-methylimidazole; 2-ethylimidazole; 2,4-diethylimidazole; 2,4-diethylimidazole; 2,4,5-trimethylimidazole; 2-benzylimidazole; 4-methylimidazole; 2-ethyl-4-methylimidazole; and 2-phenylimidazole.

One modification of the imidazoles is by addition of a $C_1$–$C_{18}$ alkyl (meth) acrylate or of acrylonitrile to the

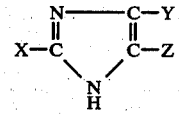

moiety. Typical alkyl acrylates utilizable include methyl acrylate, methyl methacrylate, ethyl acrylate, ethyl methacrylate, butyl acrylate, isobutyl acrylate, isobutyl methacrylate, stearylacrylate, dodecylacrylate, and 2-ethylhexyl acrylate. Also useful would be poly(meth)acrylates such as hexanedioldi(meth)acrylate, neopentylglycoldi(meth)acrylate, trimethylolpropanetri(meth)acrylate. In addition both mono and polyfunctional (meth) acrylates prepared by the reaction of epoxides with (meth)acrylic acid would also be useful. Examples of these materials would be the reaction product of Epon 828 and acrylic acid, known as Shell DRH 303, the reaction product of phenylglycidyl ether and acrylic acid and the like. In effect, any compound having an (meth)acrylate group capable of undergoing the michael type addition would be suitable. Other representative types of compounds which can be used would be acrylonitrile, acrylamide, dibutyl fumarate, hydroxyethylacrylate etc. The addition reaction is stoichiometric, i.e., on a 1:1 molar basis. The addition generally is carried out at temperatures between about 25° C. and about 200° C.

Another modification of the imidazoles is by addition of a 1,2-epoxy resin, which can be a diglycidyl ether of a bisphenol (preferably bisphenol A) or a mono-1,2-epoxy resin. The epoxy resins will have a weight per epoxy (WPE) between about 130 and about 4000. These epoxy resins are well known in the art and are generally available commercially. The addition of the epoxy group to the

group of the imidazole is stoichiometric, i.e., one mole imidazole per equivalent epoxy, although an excess of epoxy equivalents could be used. Preferably the addition is carried out in a suitable solvent, such as methyl ethyl ketone. Usually, the reaction is carried out at reflux for a total time of 1–5 hours.

Following the 1,2-epoxy addition, the solvent, if present, is stripped by distillation. Final traces of solvent are removed under vacuum.

Another modification of the imidazoles is by carbamoylization of the

moiety. This is carried out, using conventional procedures, by reaction with a lower alkyl mono- or poly-isocyanate or an aryl mono- or poly-isocyanate. Generally, the reaction is carried out at 50°–100° C. until infrared shows no -NCO remaining. Typical isocyanates include methyl isocyanate, ethyl isocyanate, propyl isocyanate, butyl isocyanate, phenyl isocyanate, hexamethylene diisocyanate, diisophorone diisocyanate and toluene diisocyanate.

After the imidazole has been modified by addition as aforedescribed, it (the adduct) is then neutralized with a lower fatty acid, such as acetic acid, propionic acid, butyric acid, lactic acid and valeric acid, a lower alkylene dicarboxylic acid, such as succinic acid or glutaric acid, or an aromatic mono or poly carboxylic acid, such as benzoic acid or phthalic acid. The neutralization is carried out on the basis of one equivalent of imidazole per 1–2 acid equivalents.

The following examples demonstrate the preparation of the curing agents or catalysts of this invention.

EXAMPLE 1

A flask was charged with 100 g. 2-ethyl-4-methyl imidazole (0.91 mole) and 167.3 g. 2-ethylhexyl acrylate (0.91 mole). The reaction mixture was heated at 130° C. for 4 hours. Gas Chromatography showed that the product contained approximately 89% of the addition product, with the remaining material being starting materials. The product was a liquid. To 100 g. of the above product (CA. 0.34 mole) was added 20.4 g. acetic acid (0.34 mole). After an initial slight exotherm, the product was cooled and yielded a viscous liquid.

EXAMPLE 2

A flask was charged with 432 g. 2-phenylimidazole (3 moles) and 552 g. 2-ethyl hexyl acrylate (3 moles). This mixture was heated at 150° C. for 13 hours. Gas Chromatography showed the product contained approximately 82% of the desired adduct plus the unreacted starting material. To 101.4 g. of the above product was added 18.6 g. acetic acid. The product was a viscous liquid.

EXAMPLE 3

A flask was charged with 962 g. EPON 1001 (epoxide equivalent weight 450–550) (2.0 equivalents epoxide) and dissolved in 700 ml. methyl ethyl ketone. To this solution there was added 220 g. 2-ethyl-4-methylimidazole (2.0 moles). Little, if any, exotherm was noted at a temperature of 30° C. The reaction mixture was then heated to 56° C. for 1.5–2 hours and then heated at reflux (about 80° C.) for 2 hours. Then began to strip out methyl ethyl ketone at atmospheric pressure. The temperature in the pot increased as the distillation proceeded. Heating was continued to 130°–140° C. and final traces of methyl ethyl ketone were removed under vacuum. The stripped product was cooled to about 125° C. and 120 g. acetic acid (2 moles) was added. Stirring was continued for about 15 minutes and the product was poured into a tray to cool. After the product was cooled to a solid it was broken up into small particles.

EXAMPLE 4

A flask was charged with 68 g. imidazole (1 mole) and dissolved in 250 ml. methyl ethyl ketone (MEK). To the solution was added 265 g. $C_{12}$–$C_{14}$ monoepoxide (1 mole) and the temperature was held at 55°–60° C. After 1.5 hours heat was increased to reflux (CA. 80° C.) and held at reflux for 1 hour. Then MEK was stripped at atmospheric pressure allowing the temperature in the reaction flask to reach 140°–150° C. Final traces of MEK were removed under vacuum. To 33.3 g. of the above product there was added 6.0 g. acetic acid. The product was a viscous liquid which partially crystallized on standing.

EXAMPLE 5

A flask was charged with 68 g. imidazole (1 mole) dissolved in 100 ml. toluene. The solution was heated to 70°–75° C. and 119 g. phenyl isocyanate (1 mole) was added. The reaction mixture was held at 70°–80° C. during the addition. After infrared showed no NCO remained, the reaction mixture was cooled, filtered, and the precipitate washed with toluene and dried. There was dissolved 18.7 g. of the above product and 5.9 g. succinic acid in MEK. Then the material was vacuum stripped to remove MEK. The product was a solid.

EXAMPLE 6

A flask was charged with 534 g. Epon 828 (3.0 equivalents epoxide) and 204 g. imidazole (3 moles) and dissolved in 600 ml. methyl ethyl ketone. The solution was heated to 50° C. and the temperature maintained under 60° C. with cooling. After the exotherm was over, the reaction was heated to reflux and held for 1 hr. Phthalic acid, 498 g. (3 moles = 6 equivalents carboxyl) was added and the solvent was then removed at atmospheric pressure during which the reaction temperature increased from 78° C. to 135° C. After the bulk of the solvent was removed, a slight vacuum was applied to remove the last traces. The produce was removed and cooled and the solified friable product was broken into small pieces.

All the catalysts of these examples were checked for catalytic effectiveness, by dissolving 0.0028 equivalents of each in a mixture of 25 g. diglycidyl ether of bisphenol A (DGEBA)(WPE=725) in 25 g. MEK. Drawdowns were made and cured in an oven for 15 minutes at 300° F. All cured to films exhibiting 160 in.lbs. reverse impact. These same solutions were checked for package stability by placing samples in an oven set at 130° F. for varying periods of time and checking both the curing and viscosity. Pertinent data are set forth in Table I.

TABLE I

| Curing Agent* | Viscosity(cps) - Days at 1300° F. | | | | | | |
|---|---|---|---|---|---|---|---|
| | 0 | 2 | 6 | 13 | 20 | 35 | 42 |
| EMI | 55 | 85 | | | Gel | | |
| EMI/HAc | 55 | 75 | — | 420 | | Gel | |
| EMI-EHA/HAc | 55 | 65 | — | 320 | 960 | 6300 | 17,300 |

Coating composition: 50% DGEBA(WPE 725):50% MEK.
Catalyst concentration: 0.0112 mole/100 g. resin.
*EMI = 2-ethyl-4-methyl imidazole.
EHA = 2-ethylhexyl acrylate.
HAc = Acetic acid.

Substantial differences in viscosity were found for these imidazole modified catalysts versus the unmodified imidazole catalyst indicating that the modified catalysts were significantly more package stable.

The invention also encompasses thermosetting powder coating compositions based on the above-described curing agents together with 1,2-epoxy resin, and optionally a flow control agent.

Conventional pigmenting materials may also be included in the formulation to impart a desirable color to the coated substrate.

The 1,2-epoxy resins utilizable in the powder coatings of this invention include diglycidyl ethers of bisphenol A, epoxy-novolac resins, and cycloaliphatic epoxy resins. Generally, they will have a WPE (weight per epoxy) between about 180 and about 4500 and, preferably between about 500 and about 2000.

The concentration ratio of curing agent will be generally between about 30:1 and about 1:1 in terms of epoxide equivalents: curing agent equivalents. Preferably, the range will be about 5–20:1.

A flow control agent is desirably incorporated into the coating compositions to aid in leveling the applied and thermoset coating, i.e., to help make the coating as smooth as or smoother than the surface of the uncoated substrate to which it is applied. Numerous flow control agents are known in the art and usable in the present compositions. An example of a commercially obtainable agent is the substance available under the trade name "Modaflo". Coating compositions of the present invention would normally include about 0.5 weight percent to about 1.5 weight percent of such leveling agent based on the weight of resin solids.

The powder coatings can be applied to the substrates by any desired powder coating process, although fluidized bed sintering (FBS), electrostatic powder coating (EPC) and the electrostatic fluidized bed (EFB) processes are preferred. The coating powders of the invention are especially well suited for the production of homogenous, firmly adherent coatings on substrates through coating by the fluidized bed or electrostatic spray methods.

In fluidized bed sintering (FBS) a preheated metal part is immersed into the coating powder of the invention, which is kept suspended by a gentle flow of air. The grain size of the powder generally ranges between 100 and 200 microns. The powder is suspended by blowing air through a porous bottom of a container so that it assumes a fluidized state. The pieces to be coated are preheated to 250° C. to 400° C. and dipped into this fluidized bed. The immersion time of the material being coated depends on the thickness of the coating that is to be produced and amounts to from 1 to 12 seconds. In general, the finished coating is prepared in a single procedure in about 3 to 7 seconds.

In the electrostatic powder coating (EPC) process, the coating powder of the invention, which normally has a grain size of under 125 microns, is carried by a stream of air into the applicator where it is charged with a voltage of 30 to 100 kV by a high-voltage direct current, and sprayed onto the electrically grounded surface of the material to be coated. Then it is baked on at a specific temperature for specific lengths of time in suitable ovens. The powder adheres to the cold work piece due to its charge because it loses its charge slowly on account of its high electrical resistance of approximately $10^{13}$ to $10^{17}$ ohm centimeters.

In the electrostatic fluidized bed (EFB) process, the two procedures are combined by mounting annular or partially annular electrodes or a wire grid within a fluidized bed containing the powder so as to produce the electrostatic charge of, for example, 50 to 100 kV. Electrically grounded surfaces, cold or heated above the sintering temperature of the powder, at for example 150° to 400° C. are briefly dipped into the powder cloud without post-sintering, or the coating may be fused by post-sintering at temperatures specific for the plastic powder.

Numerous substrates can be coated by these powder coating methods with powders of the invention, within the limits allowed by the fusing process or the heating time, as the case may be. The preferred substrates are metals, but other materials such as glasses or ceramic articles or other heat resistant materials can be coated.

It is frequently preferred to incorporate one or more pigmentary materials into the coating formulations of this invention. One such preferred pigment is titanium dioxide, but any of the well known conventional pigmenting materials can be used, such as: phthalocyanine blues and greens; red, yellow, black and brown iron oxides; chrome oxide green; natural or synthetic silicas, silicates, carbonates and so forth. Sufficient pigmentation is used to provide an opaque or colored film as needed for the desired appearance.

In order to more fully illustrate the nature of the invention and the manner of practicing the same, the following examples are presented. Measurements made on the applied coatings were obtained in accord with ASTM standard test methods as follows:

| Reverse Impact | ASTM | D-2794-69 |
| Gloss | ASTM | D-523-67 |
| Conical Mandrel Bend Elongation | ASTM | D-522-60 |
| Cross-Hatch Tape Adhesion | ASTM | D-3359-76 |

The following general procedure was used, with some slight variations, to prepare the powder coatings of this invention.

The curing agent was adapted for use by dissolving it in a fixed weight of MEK in a flask and slurrying an equal weight of rutile titanium dioxide in the solution, thereafter removing the solvent under heat and vacuum while rotating the inclined flask. All the ingredients of the recipe were initially combined in a high speed mill, such as the Welex mill, where the resinous components were rapidly fragmented into a fine powder, while becoming intimately blended with the pigment. The resulting mixture was continuously processed through a twin screw extruder at approximately 175° F. which produces a homogeneous, viscous melt while achieving good wetting and uniform dispersion of the pigment. The resulting melt was discharged onto a pair of water cooled squeeze rolls, from which the emerging cooled sheet was subsequently chipped or roughly crushed prior to pulverizing in a Condux or Micro-pul mill to particle sizes of 100 microns or less.

The powder so obtained was electrostatically spray applied under a negative potential of 50–85 kV to suitably grounded steel panels so as to produce uniform films of suitable thickness, after baking for 10 to 20 minutes at 200° F. to 400° F.

The following are illustrations of high gloss white epoxy powders prepared with certain of the curing agents of the previous examples.

EXAMPLE 7

Employing the curing agent of Example 1, a powder coating of the following composition was prepared:

| DGEBA(WPE 1105) | 344.3 grams |
| DGEBA(WPE 660-810) | 25.2 grams |
| $C_{12}$–$C_{14}$ monoepoxide (E-8) | 19.5 grams |
| Example 1 | 23.5 grams |
| Rutile Titanium Dioxide | 318.9 grams |

In this composition, the liquid $C_{12}$–$C_{14}$ monoepoxide was combined by melting nine times its weight of DGEBA epoxy resin, stirring the E-8 into the molten mass, then cooling and fragmenting the resulting friable mass. The curing agent was incorporated with a portion of the titanium dioxide as described in the general procedure, by combining 15 grams of said agent with each 85 grams of pigment.

The resulting finely divided powder, upon electrostatic spray application as described in the general procedure, showed generally good film properties when baked for 15 minutes at 270° F., or higher. Not only did 2.0–2.5 mil films successfully withstand cross-hatch tape adhesion and conical mandrel bend tests, but showed no cracking failure under 160 in.lb. reverse impact testing, while exhibiting 60° and 20° glosses of 100 and 85, respectively.

This powder also possessed superior reverse impact flexibility and gloss values in thicker film applications, as shown below, using as typical examples those cured on a schedule of 15 minutes at 300° F.

| Film thickness - mils* | Rev. Impact - In. Lb. | Gloss Values 20° | 60° |
| --- | --- | --- | --- |
| 1.9–2.2 | 160 | 85 | 100 |
| 3.3–3.7 | 160 | 91 | 100 |
| 4.3–4.7 | 132 | 91 | 100 |
| 4.8–5.2 | 148 | 93 | 100 |
| 5.2–5.5 | 124 | 95 | 100 |

*on 20 gauge Bonderite #1000 treated CRS

EXAMPLE 8

Employing the curing agent of Example 2 a high gloss white epoxy powder was prepared having the following composition:

| | |
| --- | --- |
| DGEBA(WPE 1056) | 297.0 grams |
| $C_{12}$–$C_{14}$ monoepoxide | 3.0 grams |
| Modaflo II (Flow agent - Monsanto) | 4.0 grams |
| Example 2 | 14.1 grams |
| Rutile titanium dioxide | 245.1 grams |

In this formula the $C_{12}$–$C_{14}$ monoepoxide and the liquid curing agent were incorporated following the procedure described in Example 7.

When the finely divided powder resulting from this preparation was electrostatically sprayed, followed by baking for 15 minutes at 250° F., 2.2 mil films resisted reverse impacts of 120 in.lb. or higher, while baking at 270°–330° F. yielded films which withstood 160 in.lb. reverse impact. In a series of panels baked at 300° F. and ranging in film thickness as described in Example 7, approximately the same levels of reverse impact resistance and gloss values were obtained at corresponding film thicknesses.

A unique advantage found for the curing agent of Example 2 is its ability to suppress the development of discoloration of the white film when longer cure schedules or higher cure temperatures are employed. Using the Hunter Color Difference Meter Model D25D3P, an instrument widely employed in the coatings field for such purposes, it is possible to make numerical color assessments of paint films. Specifically, it is convenient to measure the degree of redness or greenness of white coatings, as well as the blueness or yellowness. Employing the "b" values, which depict the latter color characteristic, as a means of illustrating this, the following figures disclose that the coating of Example 8, by virtue of its lower positive "b" value, discolors less than typical coatings employing other acrylated, acetic acid neutralized imidazoles, such as those based on 2-methyl imidazole, as shown below:

| 15 minute bake temperatures | "b" Value Example 8 | "b" Value Other Imidazole |
| --- | --- | --- |
| 220° F. | +0.04 | +0.03 |
| 250° F. | +0.46 | +1.06 |
| 270° F. | +0.82 | +2.71 |
| 300° F. | +2.04 | +5.10 |
| 330° F. | +3.11 | +6.92 |

EXAMPLE 9

Utilizing the curing agent of Example 3, a high gloss white epoxy powder with the following composition was prepared in the conventional manner:

| | |
| --- | --- |
| DGEBA(WPE 1055.7) | 297.0 grams |
| $C_{12}$–$C_{14}$ monoepoxide | 3.0 grams |
| Modaflo II | 4.0 grams |
| Example 3 | 23.6 grams |
| Rutile Titanium dioxide | 245.0 grams |

As in the previous examples, $C_{12}$–$C_{14}$ monoepoxide was incorporated by dissolving it as a 10% solution in molten epoxy resin, and adding the cooled product to the Welex for fragmentation and blending prior to extrusion.

The finely divided product, electrostatically spray applied, developed reverse impact values of greater than 100 in.lb. when baked at 270° F. or higher. Furthermore, this curing agent in solid form, requiring no deposition on pigment or other special treatment, also displayed superior resistance to discoloration when cured at higher temperatures, as illustrated below:

| Cure Temp. | "b" Value Example 9 | "b" Value Example 8 |
| --- | --- | --- |
| 270° F. | +1.30 | +0.82 |
| 200° F. | +3.15 | +2.04 |
| 330° F. | +4.17 | +3.11 |

EXAMPLE 10

The following high gloss white epoxy powder was prepared employing the curing agent of Example 4, having the composition shown:

| | |
| --- | --- |
| DGEBA(WPE 899.6) | 348.0 grams |
| Modaflo II | 4.5 grams |
| Example 4 | 16.6 grams |
| Rutile Titanium dioxide | 284.9 grams |

The curing agent herein employed was incorporated, as in several previous examples, by deposition on the titanium dioxide pigment from solution, via slurrying, followed by stripping of the solvent under gentle heat and vacuum.

The sprayed, cured powder from this example was characterized by reverse impact values of 100 in.lb. or more when cured for 15 minutes at 300° F. or higher. At these cure temperatures it also demonstrated outstanding gloss values of 100 both in the 20° and the 60° readings.

Although the present invention has been described with preferred embodiments, it is to be understood that modifications and variations may be resorted to, without departing from the spirit and scope of this invention, as those skilled in the art will readily understand. Such variations and modifications are considered to be within the purview and scope of the appended claims.

What is claimed is:

1. Curing agent for epoxy resins that comprise an imidazole having the formula:

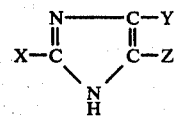

wherein X is hydrogen, methyl, ethyl, or phenyl and Y and Z are hydrogen or methyl, modified by addition of $C_1$–$C_{18}$ alkyl (meth) acrylate, by addition of a diglycidyl ether of a bisphenol, or a 1,2-monoepoxide or by carbamoylation; followed by neutralization with a lower fatty acid, or an aromatic mono-carboxylic acid.

2. The curing agent of claim 1 wherein said imidazole is 2-ethyl-4-methylimidazole.

3. The curing agent of claim 1 wherein said imidazole is 2-phenylimidazole.

4. The curing agent of claim 1 wherein said imidazole is imidazole.

5. The curing agent of claim 2 wherein modification is with 2-ethylhexyl acrylate and neutralization is with acetic acid.

6. The curing agent of claim 3 wherein modification is with 2-ethylhexyl acrylate and neutralization is with acetic acid.

7. The curing agent of claim 2 wherein modification is with a diglycidyl ether of bisphenol A having an epoxy equivalent weight of 450–550 and neutralization is with acetic acid.

8. The curing agent of claim 4 wherein modification is with a $C_{12}$–$C_{14}$ monoepoxide and neutralization is with acetic acid.

9. The curing agent of claim 4 wherein modification is by carbamoylation with phenylisocyanate.

10. A thermosetting powder coating comprising at least one 1,2-epoxy resin and a curing agent defined in claim 1.

11. The powder coating of claim 10 wherein said 1,2-epoxy resin is a mixture of a diglycidyl ether of bisphenol A having an epoxy equivalent weight of 1105, a diglycidyl ether having epoxy equivalent weight of 660–810, and a $C_{12}$–$C_{14}$ monoepoxide and said curing agent is defined in claim 5.

12. The powder coating of claim 10 wherein said 1,2-epoxy resin is a mixture of a diglycidyl ether having an epoxy equivalent weight of 1056 and a $C_{12}$–$C_{14}$ monoepoxide and said curing agent is defined in claim 6.

13. The powder coating of claim 10 wherein said 1,2-epoxy resin is a mixture of diglycidyl ether having an epoxy equivalent weight 1055.7 and a $C_{12}$–$C_{14}$ monoepoxide and said curing agent is defined in claim 7.

14. The powder coating of claim 10 wherein said 1,2-epoxy resin is a diglycidyl ether having an epoxy equivalent weight of 899.6 and said curing agent is defined in claim 1.

15. Curing agent for epoxy resins that consists essentially of an imidazole having the formula:

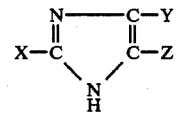

wherein X is hydrogen, methyl, ethyl, or phenyl and Y and Z are hydrogen or methyl, modified by addition of $C_1$–$C_{18}$ alkyl (meth) acrylate, by addition of a 1,2-monoepoxide or by carbamoylation; followed by neutralization with a lower fatty acid, a lower alkylene dicarboxylic acid, or an aromatic mono- or poly-carboxylic acid.

* * * * *